United States Patent [19]
Smith

[11] Patent Number: 5,861,148
[45] Date of Patent: Jan. 19, 1999

[54] OPHTHALMIC COMPOSITIONS AND PROCESS OF USING

[76] Inventor: Stewart Gregory Smith, Cloud Farm, Nine Gates Rd., Yorklyn, Del. 19736

[21] Appl. No.: 766,231

[22] Filed: Dec. 12, 1996

Related U.S. Application Data

[63] Continuation-in-part of Ser. No. 376,386, Jan. 23, 1995, abandoned.

[51] Int. Cl.⁶ .......... A61K 31/765; A61K 33/14; A61K 33/42; A61K 9/08
[52] U.S. Cl. .......... 424/78.04; 514/915
[58] Field of Search ........................ 424/78.04

[56] References Cited

U.S. PATENT DOCUMENTS

| | | | |
|---|---|---|---|
| 3,947,573 | 3/1976 | Rankin | 514/397 |
| 4,421,748 | 12/1983 | Trager et al. | 514/78 |
| 5,032,392 | 7/1991 | Varma | 514/725 |
| 5,077,033 | 12/1991 | Viegas et al. | 514/668 |
| 5,523,082 | 6/1996 | Corbiere | 424/78.04 |
| 5,529,915 | 6/1996 | Phillips et al. | 424/78.04 |

*Primary Examiner*—Peter F. Kulkosky
*Attorney, Agent, or Firm*—Herbert M. Wolfson

[57] ABSTRACT

An ophthalmic composition and process for treating blepharitis employing the composition of 0.5–10% of available nonionic surfactant in water to emulsify and remove lipids from the corneal surface.

7 Claims, No Drawings

OPHTHALMIC COMPOSITIONS AND PROCESS OF USING

CROSS REFERENCE TO RELATED APPLICATION

This application is a continuation-in-part of U.S. patent application Ser. No. 08/376,386, filed Jan. 23, 1995, now abandoned.

FIELD OF THE INVENTION

This invention relates to formulations suitable for alleviating the effects of blepharitis and relieving or preventing the discomforting condition of "dry eye."

BACKGROUND OF THE INVENTION

Blepharitis is an abnormal condition wherein the tears produced contain an excess of lipids (the oily ingredient in natural tears) and, in some cases, contain an irritating oil as well. As explained hereinafter, this oil ingredient serves to prevent evaporation of the aqueous layer that wets the corneal epithelium of the eye and helps spread the aqueous layer over the normally aqueous-resistant cornea during a blink. If excess oil is present, the lipid layer will tend to adhere to the cornea itself. If the eye is unable to clear this oil from the surface of the cornea, a "dry" area occurs on the cornea since the aqueous layer is unable to hydrate this area.

"Dry eye" can also occur because of a diminution of the quantity of tears produced and distributed through the lachrymal ducts, as well as the previously described decrease in the stability of the tear film produced. "Dry eye" acts to decrease visual acuity; produces discomfort; and eventually, if allowed to remain untreated and uncorrected, may result in permanent damage with degradation of the exposed ocular tissues, a complete breakdown of corneal tissue necessitating, in the extreme, corneal transplants.

Various compositions for treating "dry eye" have been proposed and put into use over the years. For example, the treatments employed by ancient Greek physicians for this condition dominated medical practice throughout the Middle Ages and into the nineteenth century. The selection of components for ancient collyria, or for any of the eye treatment preparations of the time, suggests either an instinctive or empirical knowledge of the composition of tears and tear films. Egg whites, very rich in albumen (a major tear protein), and goose fat, a lipid admixture, which, like meibomian lipids, becomes fluid at temperatures approximating normal body temperatures, have been used.

Use has also been made of substances which serve to induce a measure of irritation, presumably to induce reflex tearing. Such substances as alcohols, acetic acid values of vinegar, onion fermentates and the like have been utilized in this approach. Obviously, such methods are less than totally acceptable.

Other solutions offered for the alleviation of "dry eye" in more recent years, i.e., during the 19th and early 20th century, have included aqueous solutions of common table salt, glycerol, various oils and isotonic solutions of various salts, known as Ringer's and Locke's solutions.

Approximately forty years ago, the employment of aqueous solutions of inert, substituted cellulose ethers, such as methyl cellulose, was proposed, and such formulations are currently in use. Other substituted cellulose ethers, such as hydroxyethyl cellulose, hydroxypropyl methyl cellulose, and hydroxypropyl cellulose, have been subsequently utilized as polymeric components in artificial tear formulations. Each of these polymeric materials imparts high viscosity to the tear formulations, even when employed in relatively low concentrations. It has been this impartation of high viscosity to the formulations which is believed to prolong retention time of the tear substitutes in the fornices and over the preocular surface.

Recently, in U.S. Pat. No. 4,421,748 to Trager et al, a sterile hypotonic solution of 1–20 percent lecithin, preferably lecithin sulfate, and 0.1–20 percent of a cellulose-containing viscosity-adjusting agent, preferably hydroxyethyl cellulose, has been disclosed as an artificial tear formulation. Such compositions possess surface tensions approximating those of natural tears; and, if not, Trager et al. recommended the addition of 2–10 percent weight or volume of a nonionic surfactant such as polyoxyalkylene oleic ester of asorbitol anhydride to control surface tension of the artificial tear formulation.

It is an object of this invention to prevent "dry eye," or, if "dry eye" has occurred, to provide an improved formulation that quickly thereafter overcomes "dry eye" and permits the natural tears to operate in the manner that nature intended. It is a further object to avoid the use of an oil to overcome "dry eye" since adding an oil, other than the amount of oil in a natural tear, tends to overcome "dry eye" only temporarily. Other objects will be apparent hereinafter.

SUMMARY OF THE INVENTION

The objects are accomplished by treating the eye with an aqueous composition containing an effective amount of a nonionic surfactant. Applicant has found that an effective amount of surfactant may comprise anywhere from 0.5 percent by weight and volume to about 10 percent by weight and volume (hereinafter %), preferably about 1–5%, of active surfactant (not combined with oil) in the composition.

However, it should be noted that the use of any oil in the composition will reduce the effectiveness of the surfactant. The reason is that a substantial percentage of the surfactant tends to serve as a vehicle for dissolving or forming an emulsion of the oil with the aqueous layer on the cornea, thus reducing the ability of the aqueous layer to "wash" or hydrate the corneal surface. Thus, if any oil is used in the composition, then additional surfactant will be required to provide the effective amount of 0.5–10%, preferably 1–5%, of available active nonionic surfactant.

THEORY AND DETAILS OF THE INVENTION

Eighty percent of patients with red irritated eyes have blepharitis. (In fact, on slit lamp examination, approximately 70% to 80% of the population has abnormal meibomian glands and other signs of blepharitis). They try artificial tears (or are given artificial tear preparations to try by their eye specialist) and only use them briefly with minimal success.

The success is minimal based on the following reasoning. Tears are composed of three layers, aqueous, mucin and lipid layers. The mucin layer adheres to the corneal surface, which surface would repel water without the mucin in place. The aqueous layer then provides wetting of the corneal epithelium by adhering or spreading over the mucin. The outer lipid or oily layer prevents evaporation of the aqueous layer (without the lipid layer, tears would evaporate 10 to 20 times faster) and helps spread the aqueous layer during a blink. When the lipid layer adheres to the mucin layer, or to the cornea itself, rapid tear breakup occurs. If the eye is unable to clear this oil off the surface, a dry area occurs on the cornea as the aqueous material cannot hydrate it.

This is similar to oil in a frying pan. Simply running water over the oil does not remove it and the oil and the dry spot (the oil repels the water) remains. In order to remove the oil, you have to wipe it off with a cloth or use a chemical (soap) to remove it.

When patients have blepharitis, they have an excess of oil; and, in some cases, an irritating oil rather than a soothing oil is produced. The excess oil thickens the lipid layer, adheres to the cornea in certain areas, and creates dry spots as the aqueous composition is prevented from getting to the corneal surface. The patient then notes that his eye is red; his vision, blurry; and the eye starts to burn. It may then start to tear as the eye itself attempts to clear the oil from the surface. If the patient rubs the eye, more oil is expressed from the oil glands and the symptoms get worse. Some of the proteins in the aqueous layer may have surface-active properties and, thus, eventually may clear away the oil. In general, however, since you cannot wipe the oil from the cornea with a cloth, and water alone will not wash it away, clearing the eye becomes a very slow process.

However, with the composition of this invention, the problem is solved quickly and more than temporarily. The invented composition acts to dissolve away the excess lipid in the same manner as soap removes the oil or grease from the oil-covered frying pan. The action is quite prompt and by restoring the smoothness of the tear film (eliminating the depression of the tear film over the dry spot), blurring is eliminated and vision is sharpened. The surface of the cornea simply gives its shape to the tear film. As noted above, if the tear film is irregular in any way, some impairment of vision is bound to occur.

To summarize the theory of the invented solution to the problem:

Tears are composed of three (3) basic ingredients:
1. Mucin, a substance that tends to adhere to the corneal surface of the eye;
2. Water, which normally is repelled by the corneal surface, but tends to adhere to and spread within the mucin layer; and
3. a lipid e.g., body-produced lecithin and/or similar oil, which tends to cover the water-filled mucin layer, and thus reduce the evaporation rate of the aqueous system by anywhere from ten to twenty fold; and (as an oil) helps to lubricate the eye and, thus, permit the aqueous system to spread over the corneal surface during a blink of the eye.

However, if the eye is unable to periodically clear the lipid oil from the corneal surface, the lipid oil layer will actually adhere to the mucin layer or to the corneal surface itself. The aqueous layer then cannot penetrate sufficiently to form the aqueous system to hydrate the entire area of the cornea. The result is "dry eye" with accompanying discomfort in at least one irritating dry area. As stated previously, the eye becomes red; the vision, blurry; and the eye starts to burn. Rubbing the eye causes the release of more oil from the individual's oil glands; and the symptoms become worse.

The use of artificial tear compositions of the prior art at this point produces temporary relief. The artificial tear compositions tend to merely add aqueous solutions. However, the basic problem of allowing the individual's aqueous system to adhere to the mucin layer and, then cover the corneal surface does not occur if the interference by the lipid oil adherent to the oil-preferring corneal surface is not resolved.

This invention, the use of an aqueous composition containing 0.5% to 10% of an active, available nonionic surfactant overcomes "dry eye" for much longer than merely the temporary basis of the prior art compositions. However, it should be understood that the compositions of the invention may also contain a viscosity-adjusting agent, (hydroxypropyl methyl cellulose, or the like) a tonicity adjusting agent (sodium and/or potassium chloride, anhydrous dextrose, etc.), a sequestering agent (sodium citrate or the like), a preservative agent (benzalkonium chloride, sodium ethyl mercuriothiosalicylate or the like), a buffering agent (an alkali meal phosphate); etc. The invented compositions should not contain any ingredient that will detract sufficiently to lower the activity of the critical nonionic surfactant below the previously-mentioned effective percentages. Thus, the active nonionic surfactant may be used along with the commercial tear aid compositions of the prior art provided that these commercial compositions do not contain amounts of interfering substances that will tie up the nonionic surfactant to below the aforementioned effective amounts.

The interfering substances usually comprise oil substances (lecithin or other lipids) which attach to the surfactant chemically and then form emulsions with the aqueous system. As explained hereinafter, this solubilizing or emulsion-forming activity reduces the available surface activity of the surfactant. It is also important to refrain from including in the composition of this invention ionic materials, e.g., ionic polysaccharides, which form thermo-irreversible gels with the nonionic surfactant.

The preferred nonionic surfactants for use in the aqueous composition of this invention are block copolymers of ethylene oxide and propylene oxide manufactured by the BASF Company as "PLURONICS" and "Poloxamers."

The unique structure of these copolymers allow a novel approach in the design of surface-active agents. While other nonionic surfactants have a fixed hydrophobe and can effect changes in surfactant function only by altering the hydrophile, these ethylene oxide/propylene oxide block copolymers allow alteration of both the hydrophobic and hydrophilic entities. In addition, heteric structures can be introduced internally or at the end of the molecule, and the total molecular weight of the agent can be varied.

In synthesizing these surfactants, the usual first step is to create a hydrophobe of desired molecular weight. Specifically, propylene oxide is added to the two hydroxyl groups of propylene glycol. Ethylene oxide is then added to sandwich the hydrophobe between hydrophilic groups, the latter being controlled by length to constitute from 10% to 80% (by weight) of the final molecule.

The structure of these surfactants is shown below:

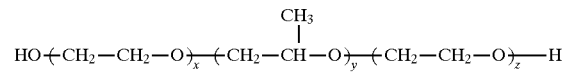

For the purpose of removing the lipid oil from the corneal surface or from the mucin layer, it is necessary to form an emulsion. To form an emulsion of the oil in water, a surfactant or emulsifier that is more soluble in water than in oil will usually be used. Hence, a predominantly hydrophilic emulsifier, e.g., PLURONIC F68, will be used. To form an emulsion of water in oil, a surfactant that is predominantly hydrophobic or lipophilic, e.g., PLURONIC L44, will be used. For the present invention, both types of surfactants have been found useful.

In the following table, the properties of the PLURONIC surfactants that I have used successfully in this invention are presented:

TABLE I

| Product | Average Molecular Wt. | Form | Melt Point °C. | Viscosity cps | Surface Tension dynes/cm | HLB |
|---|---|---|---|---|---|---|
| L44 | 2200 | liquid | 16 | 440 | 45 | 12–18 |
| F68 | 8400 | solid | 52 | 1000 | 50 | >24 |
| F87 | 7700 | solid | 49 | 700 | 44 | >24 |
| F127 | 12600 | solid | 56 | 3100 | 41 | 18–23 |
| L64 | 2900 | liquid | 16 | 850 | 43 | 12–18 |

Thus, the block copolymers of ethylene oxide and propylene oxide that I have found useful in the compositions of the invention may be hydrophilic solids or hydrophobic liquids; have a molecular weight of about 2000–13000; pour points of 16°–56° C.; viscosities of about 400–3500 cps; surface tensions of about 40–50 dynes/cm; and HLB values of 12 to greater than 24.

Other nonionic surfactants useful in this invention include the polyoxyalkylene oleic esters of sorbitol anhydrides, e.g., polysorbate 80, disodium oleamide polyethylene glycol—2 sulfosuccinate; cocoamphocarboxyl glycinate, and any of those listed in Table I on pages 253–255 of *Journal of Society Cosmetic Chemists*, Vol. 5(4), 1054, in the article entitled "Calculation of HLB Values in Non-Ionic Surfactants" by W. C. Griffin, having HLB values from 12 to greater than 24. This Griffin article is incorporated herein by reference.

In addition, the formulations may contain up to about 1% of one or more viscosity-adjusting agents; up to about 1% of one or more tonicity adjusting agents; usually about 0.3% of one or more buffering agents; and less than 0.1% of a preservative agent.

Use of the composition is conveniently performed by instilling the composition in liquid form drop-wise, into the eye or eyes of the patient. Since the eye cannot hold a full drop from a dispensing bottle, some solution will necessarily spill onto the eye lids and lashes, the sources of the excess oil in blepharitis patients. By having a liquid which is not strong enough to disrupt the tear film to the point of discomfort, but able to remove the excess oil from the tear film, the eye lids and lashes, the patient receives relief from the burning and itching of blepharitis. Prophylactic treatment for further irritation later in the day may be simultaneously performed. Thus, symptomatic relief, as well as treatment of the underlying problem, is accomplished by the use of the composition of the invention.

In summary, the use of the composition of this invention serves as a treatment for blepharitis, relieves red irritated eyes, improves visual blur caused by the presence of excess oil and thins excess oil from the ocular surface. It should be noted, however that temporary blurring of vision can occur if the drop is used and the tear film is at a normal thickness, with respect to lipids; or irritation of the eye could occur if the drop is used too often and too much lipid has been removed.

The invention will be more clearly understood by referring to the following examples:

EXAMPLE 1

The following six (6) formulations of nonionic surfactants in purified or sterile water but also containing 0.055% monobasic sodium phosphate, 0.227% anhydrous dibasic sodium phosphate, 0.6% sodium chloride, 0.075% potassium chloride, 0.003% anhydrous dextrose, 0.1% Dextran 70, 0.8% hydroxypropyl methyl chloride, 0.01% benzalkonium chloride were prepared:

A. 1% "Poloxamer" 188 (PLURONIC F68)
B. 4% "Poloxamer" 185 (PLURONIC L64)
C. 1% Disodium Oleomides
D. 4% Cocoamphocarboxyl
E. 0.1% "Poloxamer" 188 (PLURONIC F68) 0.4% "Poloxamer" 185 (PLURONIC L64) 0.2% Disodium Oleomides PEC-2 Sulfosuccinate 0.4% Cocoamphocarboxyl-glycinate
F. 1 % Polysorbate 80

When instilled into the eye of an adult, in the form of drops, "dry eye" was alleviated within 5 to 10 minutes with all formulations:

Formulation A produced no burning sensation.

Formulation B produced no stinging, but some blurring. However, the eyes felt moist and comfortable two (2) hours later.

Formulation C produced a stinging sensation upon being instilled but quite comfortable 12 hours later.

Formulation D produced some initial stinging; vision cleared but some stinging persisted.

Formulation E produced some initial stinging but vision cleared.

Formulation F produced no stinging; blurred vision for 1–3 minutes but vision cleared afterward.

It is believed that the effect on vision (blurred or clear) depended upon the initial oil concentration on the ocular surface.

EXAMPLE II

In further testing, the preferred "Poloxamer" or PLURONIC ethylene oxide-propylene oxide block copolymers were used in amounts ranging from 1 to 5% (by weight) with the following results:

G. "Poloxamer" 188, also known as PLURONIC F 68NF was used to provide a comfortable initial feeling and the eye felt comfortable for a long period of time afterwards;

H. "Poloxamer" 407, also known as PLURONIC F127 provided a comfortable initial feeling which persisted for at least two hours;

I. "Poloxamer" 237, also known as PLURONIC F87NF provided a comfortable initial feeling which lasted over one hour;

J. "Poloxamer" 124, also known as PLURONIC L 44N provided a comfortable initial feeling with some initial blurring of contact lenses, which blurring disappeared after about 15 minutes and where the experimenter experienced a significant improvement after about one hour which comfortable feeling persisted thereafter.

What is claimed is:

1. An aqueous composition to effect a significant improvement for a significant period of time in the treatment of blepharitis consisting essentially of greater than zero to about 1% of at least one tonicity-adjusting agent, greater than zero to about 0.1% of a preservative agent, greater than zero about 0.3% of at least one buffering agent, said ingredients being present in an amount of from 0.07% to 1.4% by weight, said per cent being based upon weight per volume and an amount of a nonionic surfactant comprising a block copolymer of 20–80% ethylene oxide and 80–20% propylene oxide having a molecular weight of about 2000–13000, a viscosity of about 400–3500 centipoises, a surface tension of about 40–50 dynes/centimeter and an HLB value of at least 12 in sterile water sufficient to provide 0.5–10% by weight of available nonionic surfactant.

2. A process to effect a significant improvement for a significant period of time in the treatment of blepharitis comprising (1) contacting the surface of the cornea having lipids on its surface with an aqueous composition consisting essentially of: greater than zero to about 1% of at least one viscosity-adjusting agent, greater than zero to about 0.1% of a preservative agent, greater than zero about 0.3% of at least one buffering agent, said ingredients being present in an amount of from 0.07 to 1.4% by weight, said per cent being based upon weight per volume an amount of a nonionic surfactant comprising a block copolymer of 20–80% ethylene oxide and 80–20% propylene oxide having a molecular weight of about 2000–13000, a viscosity of about 400–3500 centipoises, a surface tension of about 40–50 dynes/centimeter and all HLB value of at least 12 in sterile water sufficient to provide 0.5–10% by weight of available nonionic surfactant to dissolve said lipids on said surface of said cornea; (2) removing said composition containing dissolved lipids; and (3) permitting the mucin and aqueous layers of the natural tear to contact the complete surface of the cornea.

3. A process as in claim 2 wherein said viscosity-adjusting agent is hydroxy propyl methyl chloride.

4. A process as in claim 2 wherein said tonicity-adjusting agent is selected from the group consisting of sodium chloride, potassium chloride and dextrose.

5. A process as in claim 2 wherein said preservative agent is benzalkonium chloride.

6. A process as in claim 2 wherein said buffering agent is selected from the group consisting of monobasic sodium phosphate and anhydrous dibasic sodium phosphate.

7. A process as in claim 2 wherein the amount of said nonionic surfactant is sufficient to provide about 1–5% of available nonionic surfactant.

* * * * *